(12) United States Patent
Itoh et al.

(10) Patent No.: US 7,754,476 B2
(45) Date of Patent: Jul. 13, 2010

(54) BIOCHEMICAL REACTION CARTRIDGE

(75) Inventors: Hiroshi Itoh, Utsunomiya (JP);
Yasuyuki Numajiri, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 776 days.

(21) Appl. No.: 11/052,024

(22) Filed: Feb. 8, 2005

(65) Prior Publication Data

US 2005/0180880 A1 Aug. 18, 2005

(30) Foreign Application Priority Data

Feb. 13, 2004 (JP) ............................. 2004-036598

(51) Int. Cl.
*C12M 1/34* (2006.01)
*C12M 3/00* (2006.01)

(52) U.S. Cl. .................................................. 435/288.5
(58) Field of Classification Search ............... 435/288.5
See application file for complete search history.

(56) References Cited

U.S. PATENT DOCUMENTS

| | | | |
|---|---|---|---|
| 4,199,544 A | 4/1980 | Mühlbock et al. | 422/72 |
| 4,581,014 A * | 4/1986 | Millerd et al. | 604/80 |
| 5,323,653 A * | 6/1994 | Gruett | 73/326 |
| 5,370,842 A | 12/1994 | Miyazaki et al. | 422/82.06 |
| 5,445,934 A | 8/1995 | Fodor et al. | 435/6 |
| 5,637,469 A | 6/1997 | Wilding et al. | 435/7.21 |
| 5,856,174 A | 1/1999 | Lipshutz et al. | 435/286.5 |
| 2002/0140940 A1 | 10/2002 | Bambot et al. | 356/446 |
| 2002/0168688 A1 | 11/2002 | Parce et al. | 435/7.1 |
| 2003/0152487 A1 | 8/2003 | Holl et al. | 422/82.08 |

FOREIGN PATENT DOCUMENTS

| | | |
|---|---|---|
| JP | 7-318398 | 12/1995 |
| JP | 2832117 | 9/1998 |
| JP | 11-509094 | 8/1999 |
| JP | 2000-274375 | 10/2000 |
| WO | WO 90/09596 | 8/1990 |
| WO | WO 93/08893 | 5/1993 |
| WO | WO 97/26510 | 7/1997 |

OTHER PUBLICATIONS

A. Lueking, et al., "Protein Microarrays for Gene Expression and Antibody Screen", Analytical Biochemistry, vol. 270, Issue 1, pp. 103-111 (May 15, 1999).

* cited by examiner

*Primary Examiner*—Walter D Griffin
*Assistant Examiner*—Lydia Edwards
(74) *Attorney, Agent, or Firm*—Fitzpatrick, Cella, Harper & Scinto

(57) ABSTRACT

A biochemical reaction cartridge includes an injection port for a liquid specimen, and a chamber for containing the liquid specimen. The chamber includes at least a portion which is a transparent portion through which the liquid specimen in the chamber is visually observable externally, with the transparent portion being provided with an indicator which indicates a predetermined amount of the liquid specimen.

2 Claims, 9 Drawing Sheets

BIOCHEMICAL REACTION CARTRIDGE

FIELD OF THE INVENTION AND RELATED ART

The present invention relates to a biochemical reaction cartridge which is used by being incorporated into an apparatus for analyzing cell, microorganism, chromosome, nucleic acid, etc., in a specimen by utilizing a biochemical reaction, such as antigen-antibody reaction or nucleic acid hybridization reaction.

Most analyzers for analyzing specimens such as blood use an immunological procedure utilizing antigen-antibody reaction or a procedure utilizing nuclei acid hybridization. For example, protein such as antibody or antigen, or single-stranded nucleic acid, which specifically connects with a specimen, is used as a probe and is fixed on a surface of solid phase, such as fine particles, beads or a glass plate, thus effecting antigen-antibody reaction or nucleic acid hybridization. Then, for example, an antigen-antibody compound or double-stranded nucleic acid is detected by a labelled antigen or labeled nucleic acid, which causes a specific interaction such that a labeled material having a high detection sensitivity, such as an enzyme, a fluorescent material or a luminescent material, is supported, thus effecting detection of presence or absence of the specimen or quantitative determination of the specimen.

As an extension of these technologies, e.g., U.S. Pat. No. 5,445,934 has disclosed a so-called DNA (deoxyribonucleic acid) array wherein a large number of DNA probes having mutually different base sequences are arranged on a substrate in array form.

Further, Anal. Biochem., 270(1), pp. 103-111 (1999) has disclosed a process for preparing a protein array, like the DNA array, such that various species of proteins are arranged on a membrane filter. By using these DNA and protein arrays and the like, it has become possible to effect a test on a large number of items at the same time.

Further, in various methods of specimen analysis, in order to realize alleviation of contamination by specimen, promotion of reaction efficiency, reduction in apparatus size, and facilitation of operation, there have been also proposed disposable biochemical reaction cartridges in which a necessary reaction is performed in the cartridge. For example, Japanese Laid-Open Patent Application (JP-A) (Tokuhyo) Hei 11-509094 has disclosed a biochemical reaction cartridge, including DNA array, in which a plurality of chambers are disposed and a solution is moved by a differential pressure so as to permit a reaction such as extraction, amplification or hybridization of DNA in a specimen within the cartridge.

As a method for externally injecting a solution into the inside of such biochemical reaction cartridges, it is possible to utilize an external syringe or vacuum pump. Further, a method for moving the solution within the biochemical reaction cartridges, those utilizing gravity, capillarity, and electrophoresis are known. Further, as a compact micropump which can be provided inside of the biochemical reaction cartridge, Japanese Patent No. 2832117 has disclosed one utilizing a heat generating element, JP-A (Tokkai) 2000-274375 has disclosed one utilizing a piezoelectric element, and JP-A (Tokuhyo) Hei 11-509094 has disclosed a diaphragm pump.

As described above, it is preferable that a disposable cartridge containing a necessary solution is used from the viewpoints of prevention of secondary infection or contamination and usability but the cartridge containing a pump is expensive. For this reason, there has also been proposed a disposable biochemical reaction cartridge having a structure capable of causing a sequence of a biochemical reaction to proceed by moving a solution under the action of an external pump without containing a pump and capable of preventing the solution from flowing out of the cartridge after a user injects a specimen into the chamber.

As a method for injecting blood or the like as the specimen into the inside of the biochemical reaction cartridge, e.g., U.S. Pat. No. 6,458,545 has disclosed a method of introducing blood into a blood collecting portion by providing a blood collecting tube containing a chip with an injection needle. In addition thereto, generally, when the blood is collected from a person to be tested, the collection is performed by use of an injection syringe or a combination of a blood collecting tube with a blood is moved in a test tube, a tester injects the blood by use of the injection syringe or a pipet.

However, in the conventional biochemical reaction cartridges, an amount of the specimen necessary to cause a sequence of a biochemical reaction to proceed is not determined, so that the specimen is insufficient in amount in some cases. As a result, there arises such a problem that a test cannot be performed with high reliability.

Further, particularly, in a test using DNA from the specimen, it is necessary to effect amplification more times in order to ensure an amount of DNA required for the test. As a result, there arises such a problem that a time required for the amplification becomes long to prolong a test time.

Further, even at the time of starting a biochemical reaction in the biochemical reaction cartridge, there is no step of confirming the amount of the specimen. As a result, there also arises such a problem that the biochemical reaction is stated irrespectively of presence/absence and the amount of the specimen.

SUMMARY OF THE INVENTION

A principal object of the present invention is to solve the above described problems.

A specific object of the present invention is to provide a biochemical reaction cartridge capable of confirming an amount of a liquid specimen therein by eye observation.

According to an aspect of the present invention, there is provided a biochemical reaction cartridge, comprising:
 an injection port for a liquid specimen, and
 a chamber for containing the liquid specimen,
 wherein the chamber comprises at least a portion which is a transparent portion through which the liquid specimen in the chamber is visually observable externally, the transparent portion being provided with an indicator which is capable of comparing an amount of the liquid specimen with a predetermined amount.

According to another aspect of the present invention, there is provided a biochemical reaction cartridge, comprising:
 an injection port for a liquid specimen, and
 a chamber, for containing the liquid specimen, provided with an indicator comprising an unevenness capable of comparing an amount of the liquid specimen with a predetermined amount,
 wherein the chamber comprises at least a portion and the unevenness which are a transparent portion through which the liquid specimen in the chamber is visually observable externally.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Hereinbelow, the present invention will be described more specifically with reference to the drawings.

Embodiment 1

Figure 1:
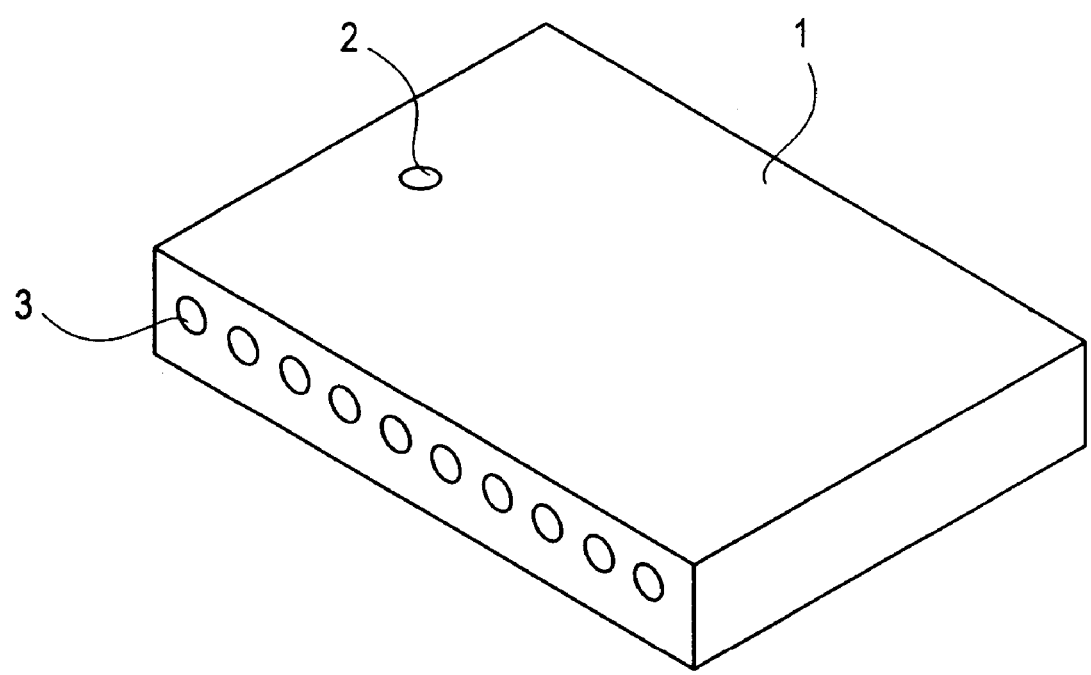
FIG. 1 is a perspective view of the biochemical reaction cartridge according to Embodiment of the present invention.

FIG. 1 is a perspective view of a biochemical reaction cartridge 1 in this embodiment. Referring to FIG. 1, on the cartridge 1, a specimen port 2 for injecting a specimen such as blood by a syringe (injector) or the like is disposed and sealed up with a rubber cap. On a side surface of the cartridge 1, there exists a plurality of nozzle ports 3 into which nozzles are injected to apply or reduce pressure in order to move a solution in the cartridge 1. A rubber cap is fixed on each of the nozzle ports 3. The other side surface of the cartridge 1 has a similar structure.

A body of the biochemical reaction cartridge 1 may comprise polymethyl methacrylate (PMMA), acrylonitrile-butadiene-styrene (ABS) copolymer, polystyrene, polycarbonate, polyester, polyvinyl chloride, etc.

Figure 2:
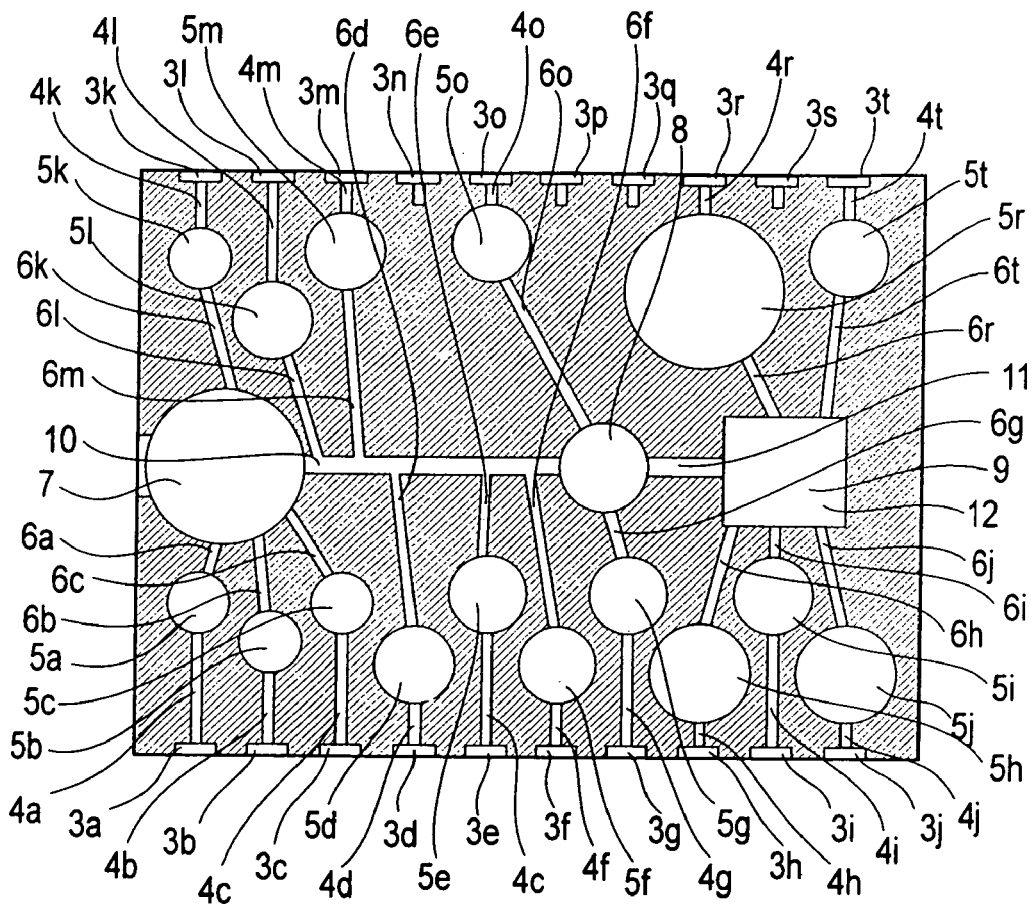
FIG. 2 is a plan view of the biochemical reaction cartridge in Embodiment 1.

FIG. 2 is a plan view (sectional view viewed from above) of the biochemical reaction cartridge 1. Referring to FIG. 2, on one side surface of the cartridge 1, 10 nozzle ports 3$a$ to 3$j$ are provided and also on the other side surface thereof, 10 nozzle ports 3$k$ to 3$t$ are provided. The respective nozzle ports 3$a$ to 3$t$ communicate with chambers 5, which are portions or sites for storing the solution or causing a reaction, through corresponding air passages 4$a$ to 4$t$, respectively.

In this embodiment, however, the nozzle ports 3$n$, 3$p$, 3$q$ and 3$s$ are not used, these nozzle ports do not communicate with the chambers 5 and are used as reserve ports. More specifically, in this embodiment, the nozzle ports 3$a$ to 3$j$ communicate with the chambers 5$a$ to 5$j$ through the passages 4$a$ to 5$j$, respectively. On the other side surface, the nozzle ports 3$k$, 3$l$, 3$m$, 3$o$, 3$r$ and 3$t$ communicate with the chambers 5$k$, 5$l$, 5$m$, 5$o$, 5$r$ and 5$t$ through the passages 4$k$, 4$l$, 4$m$, 4$o$, 4$r$ and 4$t$, respectively.

The specimen port 2 communicates with a chamber 7. The chambers 5$a$, 5$b$, 5$c$ and 5$k$ communicate with the chamber 7, the chambers 5$g$ and 5$o$ communicate with a chamber 8, and the chambers 5$h$, 5$i$, 5$j$, 5$r$ and 5$t$ communicate with a chamber 9. Further, the chamber 7 communicates with the chamber 8 via a passage 10, and the chamber 8 communicates with the chamber 9 via a passage 11. With the passage 10, the chambers 5$d$, 5$e$, 5$f$, 5$l$ and 5$m$ communicate via passages 6$d$, 6$e$, 6$f$, 6$l$ and 6$m$, respectively. At a bottom (undersurface) of the chamber 9, a square hole is provided. To the square hole, a DNA microarray 12, on which several tens to several hundreds of thousand of different species of DNA probes are arranged in high density on a surface of solid phase, such as a glass plate having a size of ca. square centimeter, with the probe surface up, is attached.

It is possible to test a large number of genes at the same time by effecting a hybridization reaction 2ith the use of the DNA microarray 12.

The DNA microarray 12 is regularly arranged in a matrix form, and an address (position determined by the number of row and the number of column on the matrix) of the DNA microarray 12 is readily read as information. The genes to be tested include, e.g., genetic polymorphism of each individual in addition to infections, viruses, bacteria and disease- associated genes.

In the chambers 5$a$ and 5$b$, e.g., a first hemolytic agent containing EDTA (ethylenediamine-tetraacetic acid) for destructing cell membrane and a second hemolytic agent containing a protein modifying agent such as a surfactant are stored, respectively.

In the chamber 5$c$, particles of magnetic material coated with silica by which DNA is adsorbed are stored. In the chambers 5$l$ and 5$m$, a first extraction cleaning liquid and a second extraction cleaning liquid which are used for purifying DNA at the time of extraction of DNA are stored, respectively.

An eluent, comprising a buffer of low-concentration salt, for eluting DNA from the magnetic particles is stored in the chamber 5$d$, a mixture liquid for PCR (polymerise chain reaction) comprising a primer, polymerise, a dNTP (deoxyribonucleotide triphosphate), a buffer, Cy-3dUTP containing a fluorescent agent, etc., is stored in the chamber 5$g$. In the chambers 5$h$ and 5$j$, a cleaning agent containing a surfactant for cleaning a fluorescence-labeled specimen DNA, which is not subjected to hybridization, and a fluorescence label is stored. In the chamber 5$i$, alcohol for drying the inside of the chamber 9 including the DNA microarray 12 is stored.

The chamber 5$e$ is a chamber in which debris other than DNA of blood accumulates, the chamber 5$f$ is a chamber in which waste of the first and second extraction cleaning liquids in the chambers 5$l$ and 5$m$ accumulate, the chambers 5$k$, 5$o$ and 5$t$ are blank chambers provided for preventing the solution to flow into the nozzle ports 3$k$, 3$o$ and 3$t$, respectively.

In this embodiment, when a tester injects blood as a specimen into the cartridge 1 through the rubber cap of the specimen port 2 by a syringe, the blood flows into the chamber 7. When this operation is performed, the cartridge 1 is placed in a substantially horizontal state.

Figure 3:
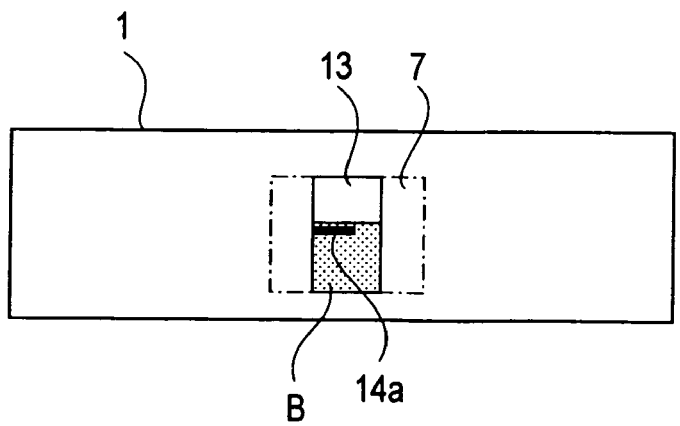
FIG. 3 is a side view of the biochemical reaction cartridge in Embodiment 1.

As shown in the side view of FIG. 3, at least a portion of the chamber 7 for containing the specimen, i.e., a transparent portion 13 constituting a part of the chamber 7 at a side surface, is formed of a transparent material so as to permit external eye observation of an amount of the specimen B. The transparent portion 13 is provided with an indicator 14$a$, consisting of a line segment, for indicating a minimum required amount of the specimen B.

Figure 4:
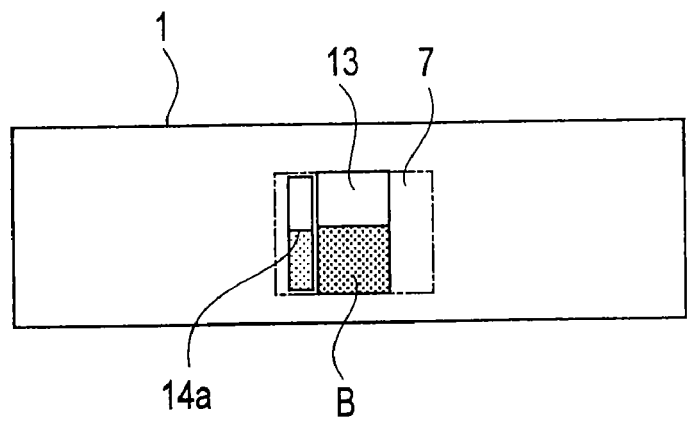
FIG. 4 is a side view of a biochemical reaction cartridge as a modified embodiment of Embodiment 1.

The indicator 14$a$ may be provided to the cartridge 1 by forming an unevenness on the cartridge 1 or may also be constituted by a color. Further, as shown in FIG. 4, a position of the indicator 14$a$ may be provided as a boundary between different colors or between different color shades. In FIGS. 3 and 4, the specimen B is contained in the cartridge 1 in an amount corresponding to a predetermined amount indicated by the indicator 14a.

When the liquid specimen such as blood is injected into the biochemical reaction cartridge describe above and the biochemical reaction cartridge 1 is set in a treatment apparatus described later, extraction and amplification of DNA or the like are performed with the cartridge 1. Further, hybridization between the amplified specimen DNA and DNA probes on the DNA microarray disposed in the cartridge and the cleaning of the fluorescence-labeled specimen DNA, which is not hybridized, and the fluorescence label are performed.

Figure 5:
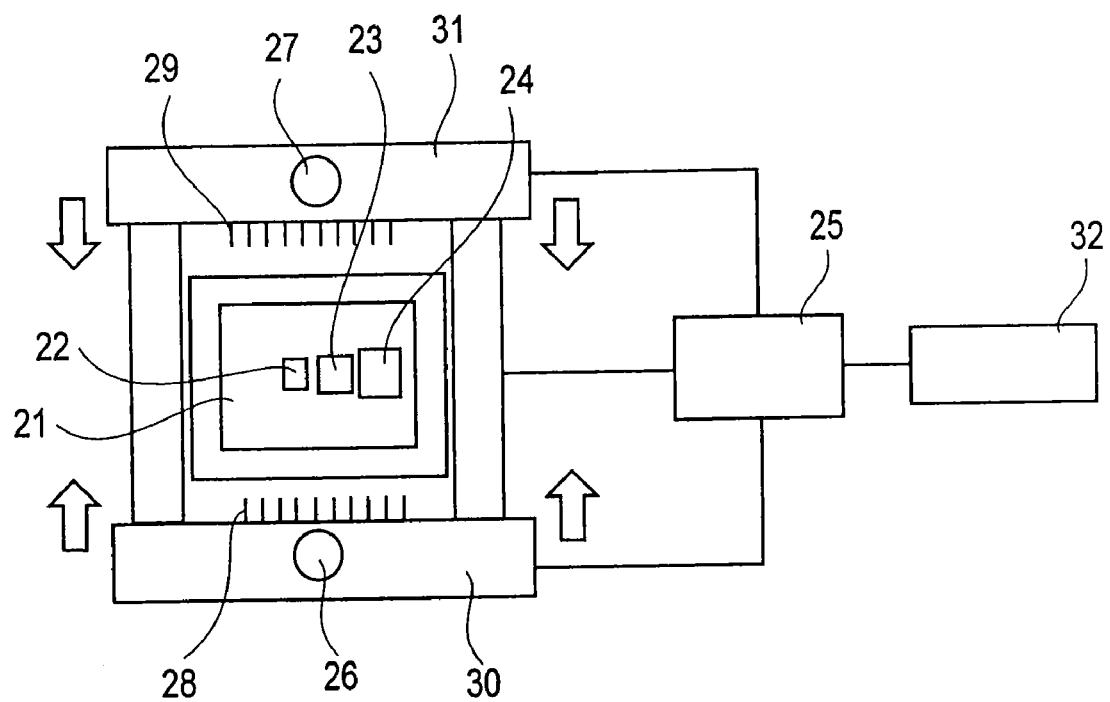
FIG. 5 is a block diagram of a treatment apparatus.

FIG. 5 is a schematic block diagram of the treatment apparatus for controlling movement of the solution within the biochemical reaction cartridge 1 and various reactions.

On a table 21, the biochemical reaction cartridge 1 is mounted. Further, on the table 21, an electromagnet 22 to be actuated at the time of extracting DNA or the like from the specimen in the cartridge 1, a Peltier element 23 for effecting temperature control at the time of amplifying DNA from the specimen through a method such as PCR (polymerase chain reaction), and a Peltier element 24 for effecting temperature control at the time of performing hybridization between the amplified specimen DNA and the DNA probe on the DNA microarray 12 within the cartridge 1 and at the time of cleaning or washing the specimen DNA which is not hybridized, are disposed and connected to a control unit 25 for controlling the entire treatment apparatus.

At both side surfaces of the table 21, an electric (motor-driven) syringe pumps 26 and 27 and pump blocks 30 and 31 each of which is a port for discharging or sucking in air by these pumps 26 and 27 and is provided with 10 pump nozzles 28 or 29 on its side surface, are disposed. Between the electric syringe pumps 26 and 27 and the pump nozzles 28 and 29, a plurality of electric switching (selector) valves (not shown) are disposed and connected to the control unit 25 together with the pumps 26 and 27. The control unit 25 is connected to an input unit 32 to which inputting by a tester is performed. The control unit 25 controls the pump nozzles 28 and 29 so that each of the respective 10 pump nozzles is selectively opened and closed with respect to the electric syringe pumps 26 and 27, respectively.

After the tester injects blood as the specimen into the chamber 7 through the rubber cap of the specimen port 2 by a syringe as defined above, the tester judges as to whether the amount of the injected specimen B reaches the indicator 14a indicating a minimum required amount for performing a biochemical reaction. When the tester judges that the specimen amount is sufficient as shown in FIG. 3, the tester places the biochemical reaction cartridge 1 on the table 21 and moves the pump blocks 30 and 31 in directions of arrows indicated in FIG. 5 by operating an unshown lever, whereby the pump nozzles 28 and 29 are injected into the cartridge 1 through the corresponding nozzle ports 3 at both side surfaces of the cartridge 1.

Further, the nozzle ports 3a to 3t are concentrated at two surfaces, i.e., both side surfaces, of the biochemical reaction cartridge 1, so that it is possible to simplify shapes and arrangements of the electric syringe pumps 26 and 27, the electric switching valves, the pump blocks 30 and 31 containing the pump nozzles, etc. Further, by effecting such a simple operation that the cartridge 1 is sandwiched between the pump blocks 30 and 31 at the same time while ensuring necessary chambers 5 and passages, it is possible to inject the pump nozzles 28 and 29 and simplify the structure of the pump blocks 30 and 31. Further, all the nozzle ports 3a to 3t are disposed at an identical level, i.e., are arranged linearly, whereby all the heights of the passages 4a to 4t connected to the nozzle ports 3a to 3t become equal to each other. As a result, preparation of the passages 4a to 4t becomes easy.

Further, in the treatment apparatus shown in FIG. 5, in the case where the length of the pump blocks 30 and 31 is increased n times the original length with respect to n biochemical reaction cartridges 1, when the n cartridges 1 are arranged in series, it is possible to perform a necessary step to all the n cartridges 1 at the same time. As a result, a biochemical reaction can be performed in the large number of biochemical reaction cartridges with a very simple apparatus structure.

Figure 6:
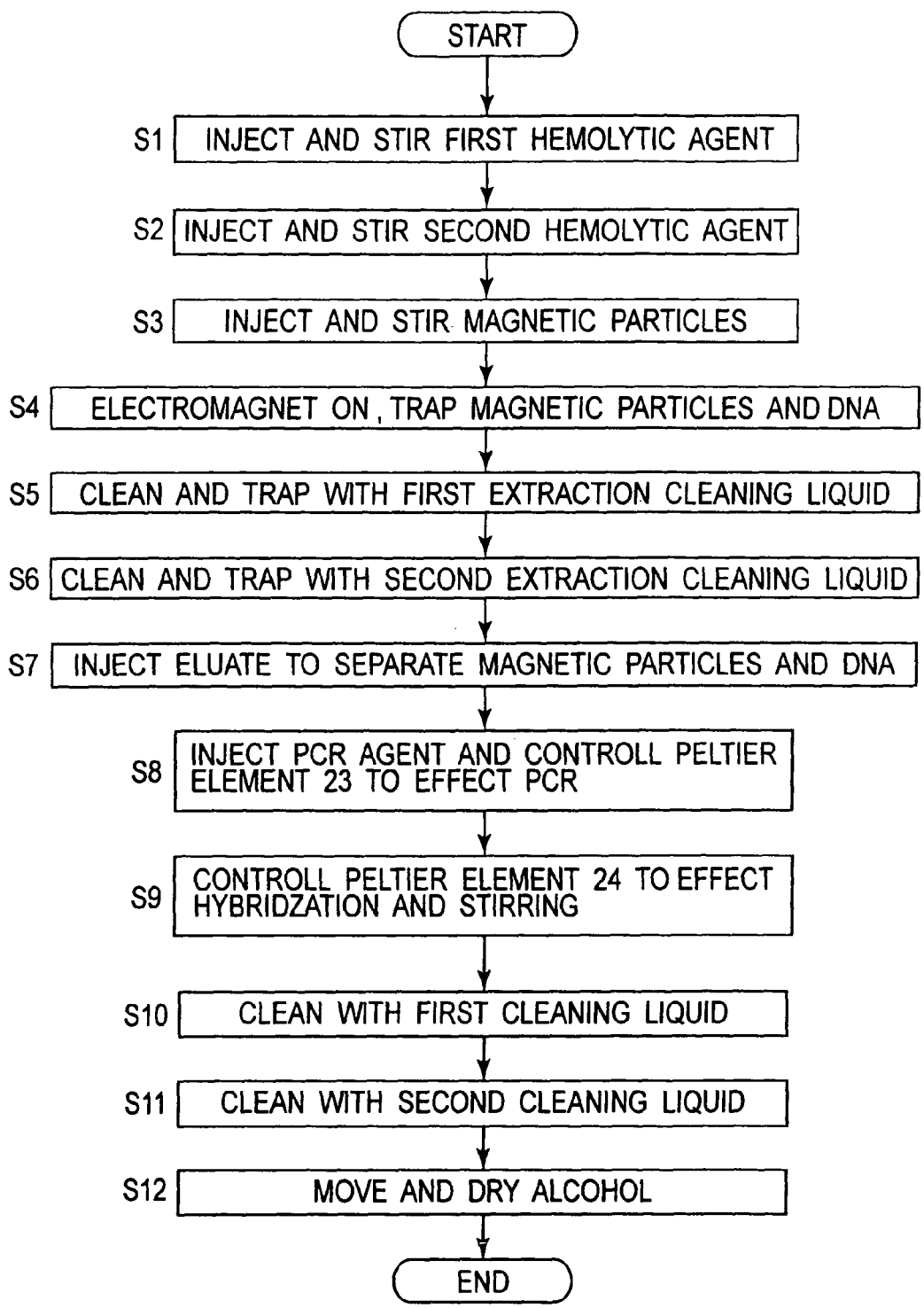
FIG. 6 is a flow chart of a treatment procedure.

Treatment starts when the tester inputs a command of procedure entry at the input unit 32. FIG. 6 is a flow chart for explaining a treatment procedure in the treatment apparatus in this embodiment.

Referring to FIG. 6, in a step S1, the control unit 25 opens only the nozzle ports 3a and 3k, and air is discharged form the electric syringe pump 26 and sucked in the cartridge 1 from the electric syringe pump 27, whereby the first hemolytic agent 1 is injected from the chamber 5a into the chamber 7 containing blood. At this time, by controlling suction of air from the pump 27 so as to start 10 to 200 msec after initiation of air discharge from the pump 26, the solution can flow smoothly without causing splash or scattering thereof at its leading end although it depends on a viscosity of the hemolytic agent and a resistance of the passage.

As described above, by shifting timing of supply and suction of air so as to control a manner of pressure application and pressure reduction, it is possible to cause the solution to flow smoothly. In a preferred embodiment, the solution can be caused to flow further smoothly by effecting such a control that a degree of suction of air by the electric syringe pump 27 is linearly increased from the initiation of air discharge from the pump 26.

The air supply control can be readily realized by using the electric syringe pumps 26 and 27. More specifically, after only the nozzle ports 3a and 3o are opened, discharge and suction of air are repeated alternately by the pumps 26 and 27 to cause repetitive flow and flowback of the solution of the chamber 7 in the passage 10, thus stirring the solution. Alternatively, the solution can be stirred while continuously discharging air from the pump 27 to generate bubbles.

Figure 7:
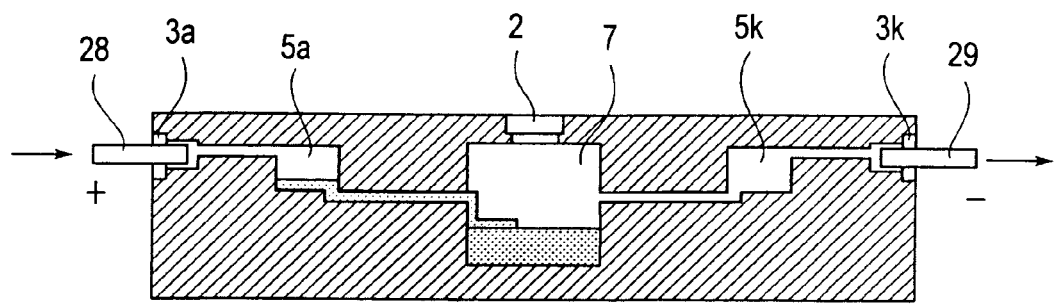
FIGS. 7 and 8 are views for explaining actions of chambers.

FIG. 7 is an explanatory view of an action of chambers 5a, 7 and 5k shown in FIG. 2, and shows such a state that the nozzle port 3a is pressurized by injecting therein the pump nozzle 28 and the nozzle port 3k is reduced in pressure by injecting therein the pump nozzle 29, whereby the first hemolytic agent in the chamber 5a flows into the chamber 7.

Referring again to the flow chart shown in FIG. 6, in a subsequent step S2, only the nozzle ports 3b and 3k are opened and the second hemolytic agent in the chamber 5b is caused to flow into the chamber 7 in the same manner as in the case of the first hemolytic agent. Similarly, in a step S3, the magnetic particles in the chamber 5c are caused to flow into the chamber 7. In the steps S2 and S3, stirring is performed in the same manner as in the step S1. In the step S3, DNA resulting from dissolution of cells in the steps S1 and S2 attaches to the magnetic particles.

Thereafter, in a step S4, an electromagnet 22 is turned on and only the nozzle ports 3e and 3k are opened. Then, air is discharged from the electric syringe pump 27 and sucked in from the pump 26 to move the solution from the chamber 7 to the chamber 5e. At the time of movement, the magnetic particles and DNA are trapped in the passage 10 on the electromagnet 22. The suction and discharge by the pumps 26 and 27 are alternately repeated to reciprocate the solution two times between the chambers 7 and 5e, whereby a trapping efficiency of DNA is improved. The trapping efficiency can be further improved by increasing the number of reciprocation. In this case, however, it takes a longer treating time by that much.

As described above, DNA is trapped in a flowing state on such a small passage having a width of about 1-2 mm and a height of about 0.2-1 mm by utilizing the magnetic particles, so that DNA can be trapped with high efficiency. This is also true for RNA and protein.

Then, in a step S5, the electromagnet 22 is turned off, and only the nozzle ports 3f and 3l are opened. Thereafter, air is discharged from the electric syringe pump 27 and sucked in from the pump 26 to move the first extraction cleaning liquid from the chamber 5l to the chamber 5f. At this time, the magnetic particles and DNA trapped in the step S4 are moved together with the extraction cleaning liquid, whereby cleaning is performed. After the reciprocation of two times is performed in the same manner as in the step S4, the electromagnet 22 is turned on, and the reciprocation of two times is similarly performed to recover the magnetic particles and DNA in the passage 10 on the electromagnet 22 and return the solution to the chamber 5l.

In a step S6, cleaning is further performed in the same manner as in the step S5 by using the second extraction cleaning liquid in the chamber 5m in combination with the nozzle ports 3f and 3m.

In a step 7, only the nozzle ports 3d and 3o are opened while the electromagnet 22 is kept on, and air is discharged from the pump 26 and sucked in from the pump 27, whereby the eluent in the chamber 5d is moved to the chamber 8.

At this time, the magnetic particles and DNA are separated by the action of the eluent, so that only the DNA is moved together with the eluent to the chamber 8, and the magnetic particles remain in the passage 10. Thus, extraction and purification of the DNA are performed. As described above, the chamber containing the extraction cleaning liquid and the chamber containing waste liquid after the cleaning are separately provided, so that it becomes possible to effect extraction and purification of the DNA in the biochemical reaction cartridge 1.

Next, in a step S8, only the nozzle ports 3g and 3o are opened, and air is discharged from the electric syringe pump 18 and sucked in from the pump 19 to cause the PCR agent in the chamber 5g to flow into the chamber 8. Further, only the nozzle ports 3g and 3t are opened, and air discharge and suction by the pumps 26 and 27 are repeated alternately to cause repetitive flow and flowback of the solution of the chamber 8 in the passage 11, thus stirring the solution. Then, the Peltier element 23 is controlled to retain the solution in the chamber 8 at 96° C. for 10 min. Thereafter, a cycle of heating at 96° C./10 sec, 55° C./10 sec, and 72° C./1 min. is repeated 30 times, thus subjecting the eluted DNA to PCR to amplify the DNA.

In a step S9, only the nozzle ports 3g and 3t are opened, and air is discharged from the electric syringe pump 26 and sucked in from the pump 27 to move the solution in the chamber 8 to the chamber 9. Further, by controlling the Peltier element 24, the solution in the chamber 9 is kept at 45° C. for 2 hours to effect hybridization. At this time, discharge and suction of air by the pumps 26 and 27 are repeated alternately to move the solution between the chamber 9 and the passage 6t, which effects stirring the solution.

In a step S10, while keeping the temperature at 45° C., only the nozzle ports 3h and 3r are opened, and air is discharged from the electric syringe pump 26 and sucked in from the pump 27 to cause the first cleaning liquid in the chamber 5h to flow into the chamber 5r through the chamber 9 while moving the solution in the chamber 9 to the chamber 5r. The suction and discharge by the pumps 26 and 27 are repeated alternately to reciprocate the solution two times between the chambers 5h, 9 and 5r and finally return the solution to the chamber 5h. Thus, the fluorescence-labeled specimen DNA and the fluorescence label which are not hybridized are cleaned.

Figure 8:
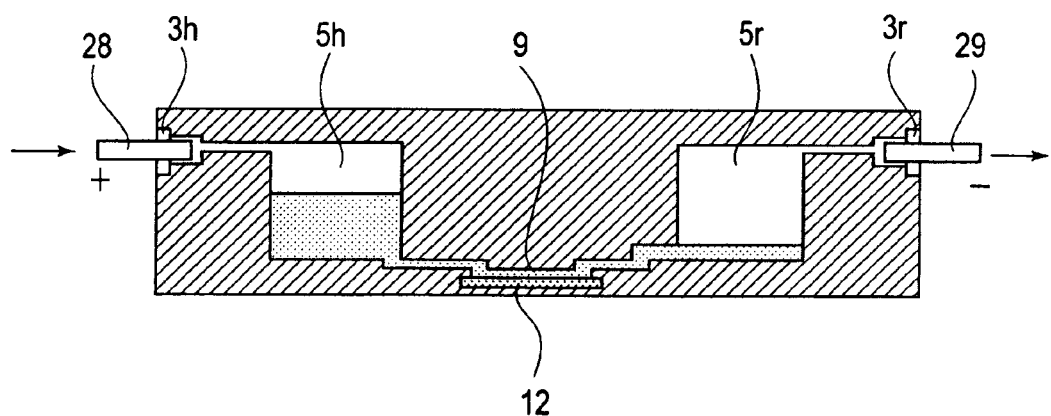

FIG. 8 is an explanatory view of an action of the chambers 5h, 9 and 5r shown in FIG. 2. The cartridge 1 is pressurized by injecting the pump nozzle 28 into the nozzle port 3h and is reduced in pressure by injecting the pump nozzle 29 into the nozzle port 3r. FIG. 8 illustrates such a state that the first cleaning liquid is caused to flow into the chamber 5r through the chamber 9.

Referring again to the flow chart of FIG. 6, in a step S11, while keeping the temperature at 45° C., the cleaning is further effected in the same manner as in the step S10 by using the second cleaning liquid in the chamber 5j in combination with the nozzle ports 3; and 3r, and the solution is finally returned to the chamber 5j. As described above, the chambers 5h and 5j containing the cleaning liquids and the chamber 5r containing waste liquid after the cleaning are separately provided, so that it becomes possible to effect cleaning of the DNA microarray 12 in the biochemical reaction cartridge 1.

In a step 12, only the nozzle ports 3i and 3r are opened, and air is discharged from the electric syringe pump 26 and sucked in from the pump 27 to move alcohol in the chamber 5i to the chamber 5r through the chamber 9. Thereafter, only the nozzle port 3i and 3t are opened, and air is discharged from the pump 26 and sucked in from the pump 27 to dry the chamber 9.

When the tester operates a lever (not shown), the pump blocks 30 and 31 are moved away from the biochemical reaction cartridge 1. As a result, the pump nozzles 28 and 29 are removed from the nozzle ports 3 of the cartridge 1. Then, the tester mounts the cartridge 1 in a reader for DNA array, such a known scanner to effect measurement and analysis.

In this embodiment, the transparent portion 13 is provided with the indicator 14a which indicates a required amount of the specimen B. However, in order to improve visibility, e.g., the transparent portion 13 may also be provided with an optical member such as a lens so as to magnify the specimen B and the indicator 14a.

In this embodiment, moving mean for moving the specimen, a reagent, a mixture thereof, or a reaction liquid, contained in the cartridge 1 is disposed outside the cartridge 1 but may be integrally disposed in the cartridge 1.

Further, the transparent portion 13 is not necessarily completely transparent but may be semitransparent so long as the specimen is visually observable. Further, when the cartridge 1 itself has such a transparency that it is visually observable from the outside thereof, it is not necessary to provide the cartridge 1 with a particular area as the transparent portion.

Embodiment 2

In Embodiment 1, the indicator 14a indicates the minimum required amount (lower limit). In this embodiment, in addition to the indicator 14a, the transparent portion 13 is provided with an indicator 14b indicating a maximum required amount (upper limit). In this regard, when the specimen is contained in the chamber 7 in an amount which is not less than the lower limit, there is no problem since the number of amplification for ensuring a required amount of DNA can be decreased. However, injection of the specimen in an amount which excessively exceeds the upper limit is not desirable from a viewpoint of a burden on a person to be tested. Further, there is a possibility that the specimen overflows the chamber 7. Accordingly, it is necessary to provide the indicator 14b for indicating the upper limit.

Embodiment 3

Figure 9:
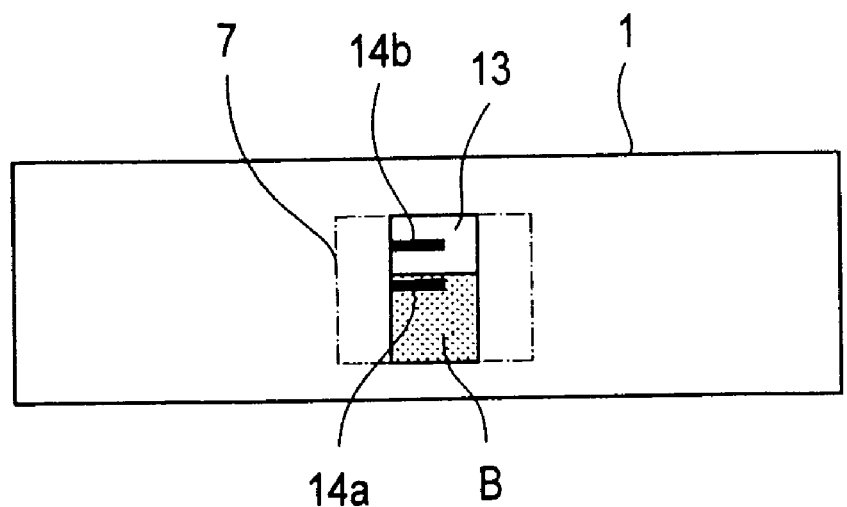
FIGS. 9-12 are side views of biochemical reaction cartridges in Embodiments 2, 3, 4 and 5, respectively.

In Embodiment 2, indication of the upper limit and the lower limit is performed by two line segments as the indicators 14b and 14a as shown in FIG. 9.

Figure 10:
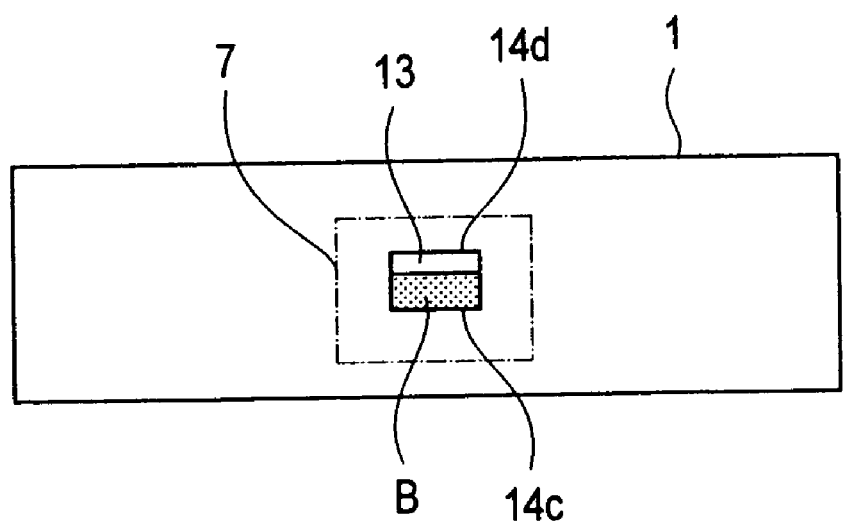

In this embodiment, as shown in FIG. 10, an upper limit boundary and a lower limit boundary of the transparent portion 13 are given by an upper indicator 14d and a lower indicator 14c, respectively. Alternatively, the upper and lower limit boundaries may have such a transparency that the tester can readily identify the specimen by eye observation.

Embodiment 4

In this embodiment, a shape of the chamber 7 is partially deformed by, e.g., cutting it outward at positions corresponding to the upper limit and the lower limit, to provide indicators 14f and 14e which are visually observable so as to permit visual identification of the specimen.

Figure 11:
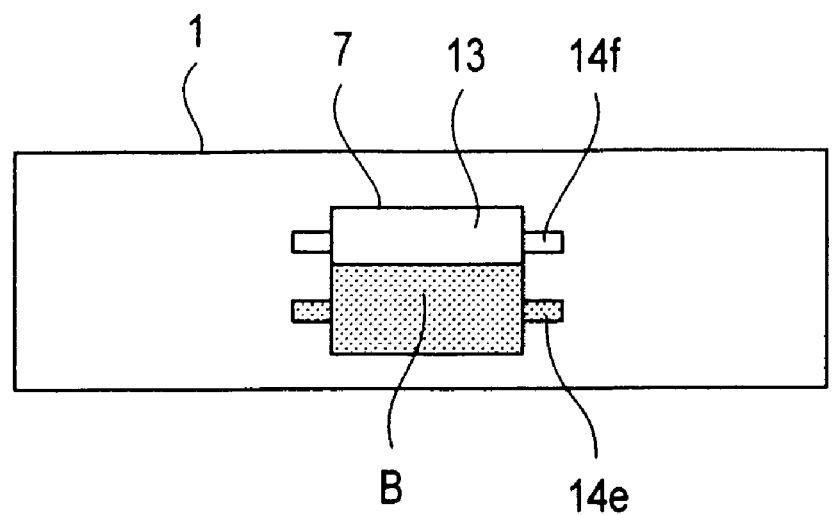

More specifically, in FIG. 11, the amount of specimen is more than the lower limit and is less than the upper limit. In this case, the specimen amount exceeds the minimum required amount indicated by the indicator 14e, so that the specimen B extends from an ordinary chamber area to the outward portion as the indicator 14e. As a result, the tester can easily confirm that the amount of specimen exceeds the minimum required amount indicated by the indicator 14e. Further, the specimen B does not reach the indicator 14f indicating the maximum required amount, so that the specimen B cannot be observed at the portion as the indicator 14f. As a method of deforming the shape of the chamber 7, the indicator corresponding portions may be extended outward as shown in FIG. 11 or may be cut inward.

Incidentally, the positions of the upper and lower limits shown in FIGS. 10 and 11 are depicted as those for easy understanding, thus being not strict positions corresponding to those shown in FIG. 7.

Embodiment 5

Figure 12:
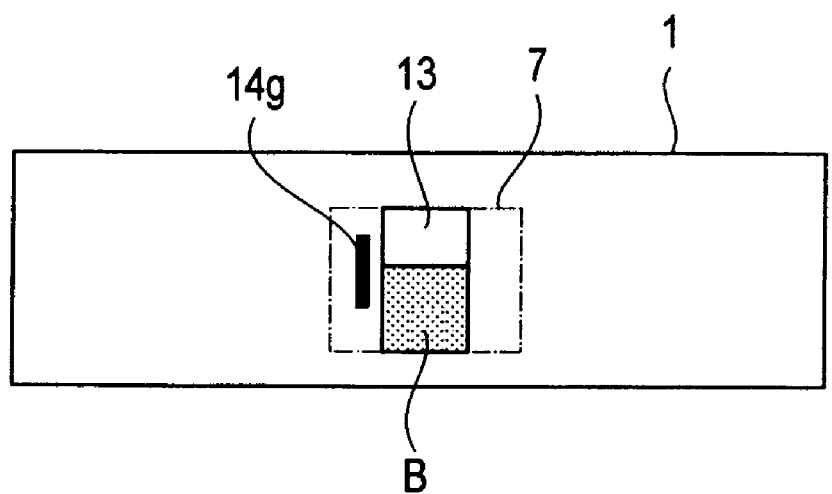

In this embodiment, as shown in FIG. 12, an area between the upper and lower limits is indicated by a vertical bar indicator 14g. This indicator 14g may also be provided by creasing a difference in level (or steps) on the surface of the cartridge 1 at positions corresponding to the upper and lower limits.

Embodiment 6

In the above described embodiments, the amount of specimen B is observed from the side surface of the cartridge 1.

In this embodiment, the specimen amount is observed from above the cartridge 1. For example, as shown in FIGS. 13(a) to 13(d), the shape of the chamber 7 is changed so that right and left projection portions (outward extended portions) have different lengths in a vertical direction, thus permitting confirmation of the specimen amount.

Each of FIGS. 13(a) to 13(d) includes a plan view (left view) and a side view (right view) of the chamber 7 in the cartridge 1.

In each of these figures, the cartridge 7 has a visually observable transparent structure at an upper portion thereof, and other portions including the specimen port 2 are not shown. The chamber 7 is provided with the right and left projection portions at both side surfaces thereof. The left projection portion is used as an indicator 14h which has a vertically long length and indicates the lower limit. The right projection portion is used as an indicator 14i which has a vertically short length to have a bottom portion located higher than that of the indicator 14h, thus indicating the upper limit.

Figure 13:
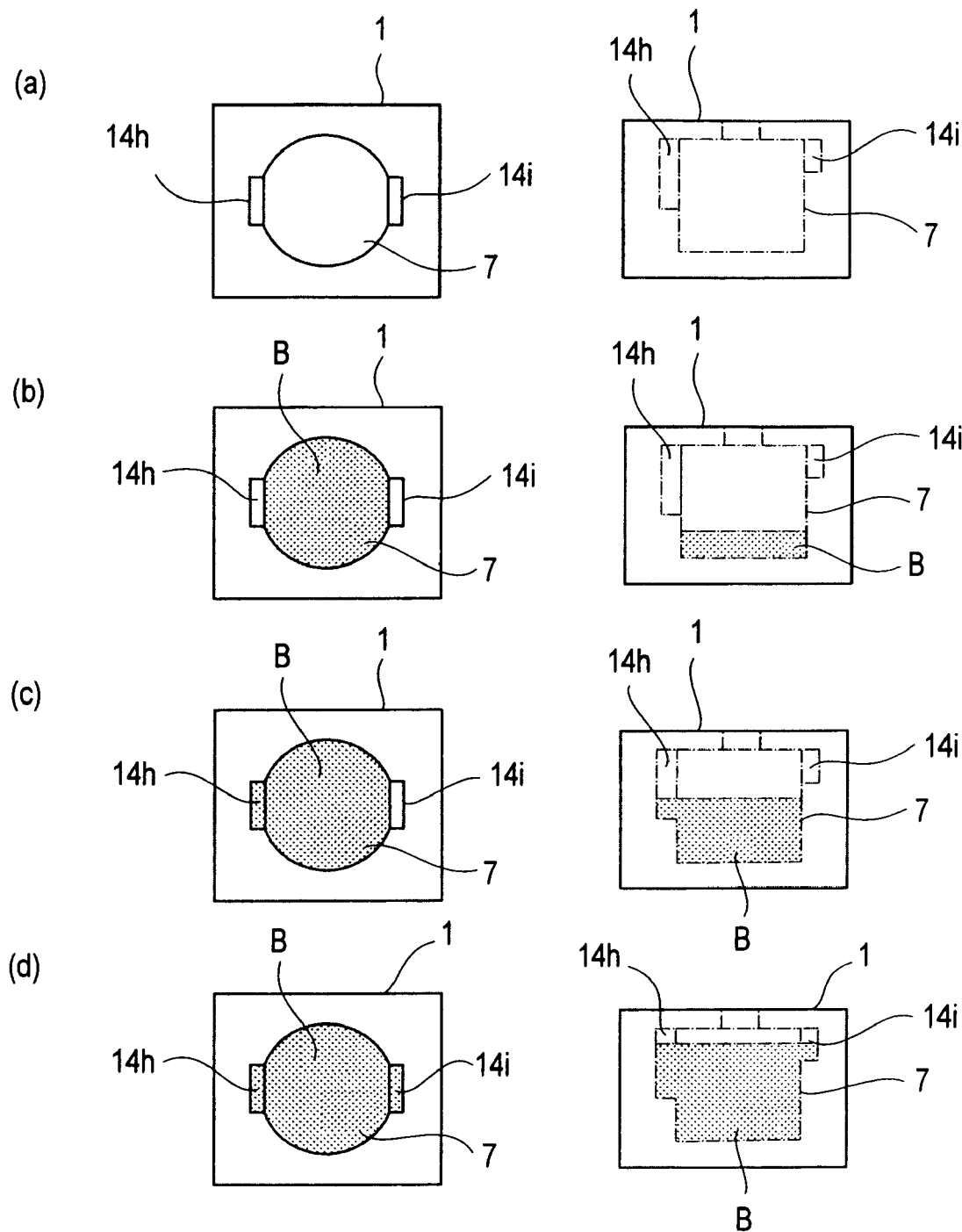
FIGS. 13($a$) to 13($d$) and 14 are explanatory views in Embodiments 6 and 7, respectively.

Referring to FIGS. 13(a) to 13(d), FIG. 13(a) shows such a state that the specimen B is not contained in the chamber 7. When the specimen B is injected into the chamber 7, the amount of the specimen B is increased, through a state shown in FIG. 13(b), to exceed the lower limit indicated by the indicator 14h. At this time, as shown in FIG. 13(c), the specimen B contained in the indicator 14h (left projection portion) is observed by the tester, so that the tester can confirm that the amount of specimen B reaches the lower limit. When the specimen B is further injected into the chamber 7, the specimen B reaches the indicator 14i indicating the upper limit as shown in FIG. 13(d). At this time, the specimen B contained in the indicator 14i (right projection portion) is observed by the tester, so that the tester can confirm that the amount of specimen B reaches the upper limit.

In this embodiment, the entire chamber 7 is visually observable but only the indicators 14h and 14i may be made visually observable.

Embodiment 7

Figure 14:
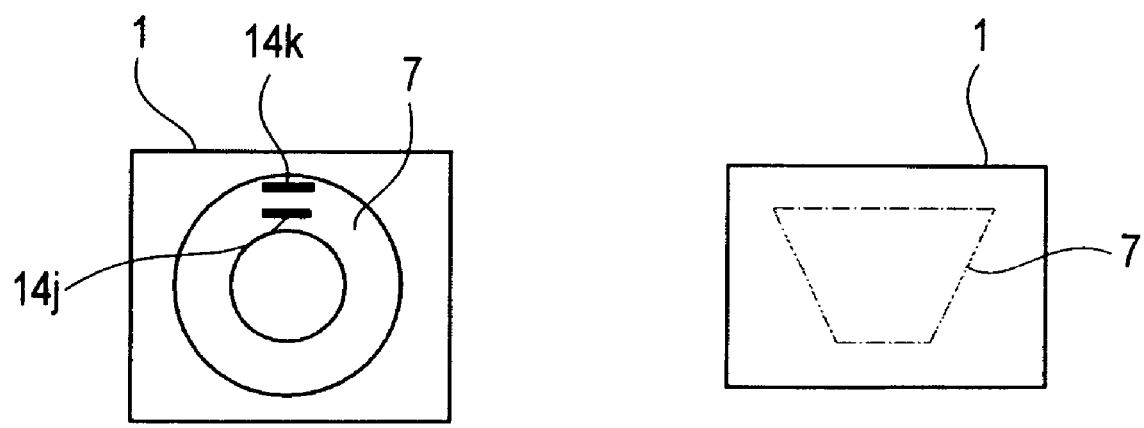

In this embodiment, as shown in FIG. 14 including a plan view (left view) and a side view (right view), the shape of the chamber 7 is changed in such a truncated cone shape that a diameter at an upper surface is larger than that at a lower surface, so that a liquid level of the specimen B is gradually increased as the specimen B is injected into the chamber 7.

At an upper surface having a transparent structure of the chamber 7, as shown in the plan view of FIG. 14, an indicator 14j which is consisting of a line segment and indicates the lower limit of specimen and an indicator 14k which is consisting of a line segment and indicates the upper limit of specimen are provided. As a result, the tester can readily confirm the amount of specimen B through the transparent upper surface of the chamber 7.

In this embodiment, the entire upper surface of the chamber 7 has a transparent structure but only portions corresponding to the indicators 14j and 14k may be made transparent and other portions may be made opaque. By doing so, an appropriate amount of specimen B can be judged when the specimen B is present in the transparent indicator 14j or 14k.

As described hereinabove, according to the present invention, it is possible to provide a biochemical reaction cartridge which permits confirmation of the amount of specimen in the chamber by eye observation.

While the invention has been described with reference to the structures disclosed herein, it is not confined to the details set forth and this application is intended to cover such modifications or changes as may come within the purposes of the improvements or the scope of the following claims.

This application claims priority from Japanese Patent Application No. 036598/2004 filed Feb. 13, 2004, which is hereby incorporated by reference.

What is claimed is:

1. A biochemical reaction cartridge for effecting a biochemical reaction therein, comprising:
   an injection port for a liquid specimen; and
   a chamber for containing the liquid specimen;
   wherein said chamber comprises at least a transparent portion through which the liquid specimen in said chamber is visually observable externally in a direction substantially perpendicular to a liquid surface of the liquid specimen, and wherein the transparent portion is provided with an indicator which is capable of comparing an amount of the liquid specimen with a predetermined amount with respect to the direction perpendicular to the liquid surface of the liquid specimen.

2. A biochemical reaction cartridge for effecting a biochemical reaction therein, comprising:

an injection port for a liquid specimen; and a chamber for containing the liquid specimen;

wherein said chamber comprises a transparent portion through which unevenness in the liquid specimen in said chamber is visually observable externally in a direction substantially perpendicular to a liquid surface of the liquid specimen, and wherein the transparent portion is provided with an unevenness indicator which is capable of comparing an amount of the liquid specimen with a predetermined amount with respect to the direction perpendicular to the liquid surface of the liquid specimen.

* * * * *